US00PP15459P2

(12) United States Plant Patent
Trees

(10) Patent No.: US PP15,459 P2
(45) Date of Patent: Dec. 28, 2004

(54) ***NEMESIA* PLANT NAMED 'BALARCOMWHIT'**

(50) Latin Name: *Nemesia caerulea*
Varietal Denomination: Balarcomwhit

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/740,741

(22) Filed: Dec. 19, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,811 P2 * 7/2002 Jones ..... Plt./263

OTHER PUBLICATIONS

UPOV ROM GITIM Computer Database, GTI Jouve Retrieval Software 2004/02 Citation(s) for 'Balarcomwhit'.*

* cited by examiner

*Primary Examiner*—Kent Bell
*Assistant Examiner*—W C Haas
(74) *Attorney, Agent, or Firm*—Wood, Phillips, Katz, Clark & Mortimer

(57) ABSTRACT

A new and distinct cultivar of *Nemesia* plant named 'Balarcomwhit', characterized by its white-colored flowers, medium green-colored foliage, and upright and spreading growth habit.

1 Drawing Sheet

Latin name of genus and species of plant claimed: *Nemesia caerulea.*
Variety denomination: 'Balarcomwhit'.

BACKGROUND OF THE INVENTION

The present invention relates to a new and distinct cultivar of *Nemesia* plant botanically known as *Nemesia caerulea* and hereinafter referred to by the cultivar name 'Balarcomwhit'.

The new cultivar was developed by the inventor in a controlled breeding program during October 2000, at Arroyo Grande, Calif. The objective of the breeding program was the development of *Nemesia* cultivars with a well-branched, spreading growth habit, unique flower colors and continuous flowering.

The new cultivar resulted from the open pollination of the *Nemesia caerulea* cultivar 'Valley Heart White' (not patented) characterized by its light pink-colored flowers, medium green-colored foliage and compact, branching habit. The new cultivar was discovered and selected as a single flowering plant among the progeny of the above open pollination by the inventor during January 2001, in a controlled environment at Arroyo Grande, Calif. and was initially designated '712-3'.

Asexual reproduction of the new cultivar by terminal stem cuttings taken since January 2001 at Arroyo Grande, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was found that the cultivar of the present invention:

1. Exhibits white-colored flowers,
2. Forms medium green-colored foliage, and
3. Exhibits a compact, well-branched growth habit.

Plants of the new cultivar differ from plants of the female parent primarily in flower color.

Of the many *Nemesia* cultivars known to the inventor, the most similar to 'Balarcomwhit' is the cultivar 'Pensug' (U.S. Plant Pat. No. 12,811). However, in side by side comparisons, plants of the new cultivar differed from plants of 'Pensug' in the following characteristics:

1. Plants of the new cultivar are less floriferous than plants of 'Pensug'.
2. Plants of the new cultivar exhibit leaves of a different shape than plants of 'Pensug'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the values cited in the detailed description, which accurately describe the colors of 'Balarcomwhit'. The plants were grown in 10 cm pots for 10 weeks in a greenhouse at West Chicago, Ill.

DETAILED BOTANICAL DESCRIPTION

Figure 1:
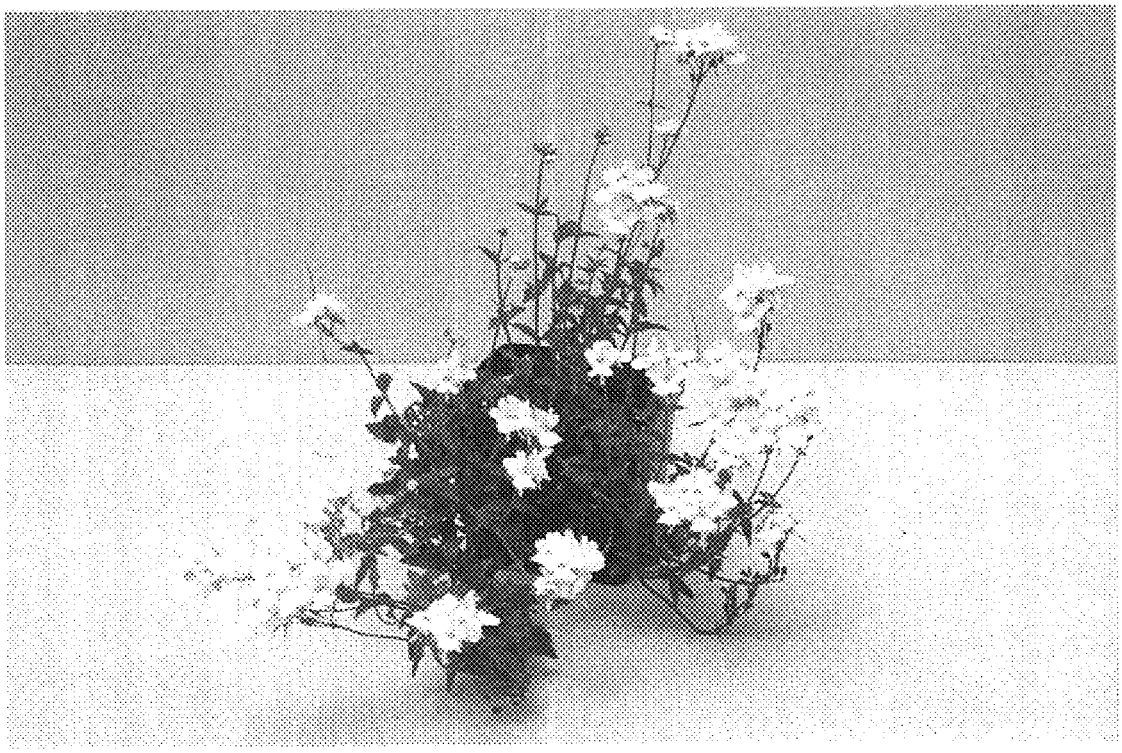
FIG. 1 illustrates a side view of the overall growth and flowering habit of 'Balarcomwhit'.
Figure 2:
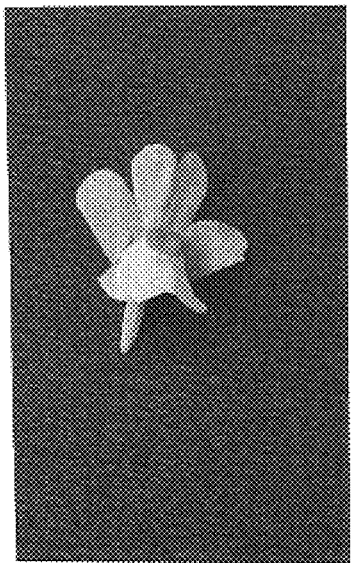
FIG. 2 illustrates a close-up view of an individual flower of 'Balarcomwhit'.

The chart used in the identification of colors described herein is The R.H.S. Colour Chart of The Royal Horticultural Society, London, England, 1995 edition, except where general color terms of ordinary significance are used. The color values were determined on May 14, 2003. The readings were taken between 1:00 and 3:00 p.m. under natural light conditions. The plants were produced from cuttings taken from stock plants and were grown in a double polycarbonate-covered greenhouse in West Chicago, Ill. under conditions comparable to those used in commercial practice. The plants were grown in 10 cm pots for 12 weeks while utilizing a soilless growth medium. Greenhouse temperatures were maintained at approximately 65°–75° F. (18°–24° C.) during the day and approximately 50°–60° F. (10°–15° C.) during the night. Greenhouse light levels were maintained at approximately 4,000 to 7,000 footcandles during the day.

Botanical classification: *Nemesia caerulea,* cultivar 'Balarcomwhit'.

Parentage: Open pollination of *Nemesia caerulea* cultivar 'Valley Heart White'.

Propagation:

*Type cutting.*—Terminal stem.

*Time to initiate roots.*—Approximately 7 to 10 days.

*Time to develop roots.*—Approximately 21 to 28 days.

*Root description.*—Fine and fibrous.

*Rooting habit.*—Freely branching.

Plant description:

*Habit of growth.*—Moderately vigorous with good branching. An average of 10 primary branches and 70 secondary lateral branches develop after pinching.

*Form.*—Upright and outwardly spreading.

*Size.*—A mature plant, 12 weeks after the planting of a rooted cutting, commonly measures approximately 21.7 cm in height from soil level to top of foliage and approximately 41.1 cm in diameter (area of spread).

*Primary branch.*—Shape: Tetragonal. Appearance: Wiry. Strength: Moderate. Length: Approximately 18.1 cm. Diameter: Approximately 1 mm. Texture: Moderately pubescent. Internode length at middle of branch: Approximately 2.6 cm. Color: Darker than 144A.

*Secondary lateral branches.*—Shape: Tetragonal. Length: Approximately 9 cm. Diameter: approximately 1 mm. Color: 144A.

*Foliage.*—Type: Single. Fragrance: None. Arrangement: Opposite. Quantity per branch: Approximately 10. Orientation to stem: Acute. Shape: Ovate. Margin: Micro serrate. Apex: Acute. Base: Decurrent. Length of leaf taken from middle of branch: Approximately 2.9 cm. Leaf width: Approximately 1.3 cm. Texture of upper and lower surfaces: Glabrous. Venation pattern: Pinnate. Color of upper and lower surfaces of young foliage: 144A. Color of mature foliage: Upper surface: 137A with venation of N144C. Lower surface: 137C with venation of N144C.

Flowering description:

*Flowering habit.*—Freely flowering.

*Natural flowering season.*—Year round in greenhouse environment and spring through autumn in outdoor garden.

*Inflorescence type/description.*—Terminal clusters. Length: 6 cm. Width: 3 cm. Number per plant: Approximately 10.4 fully open clusters and 16.8 developing clusters per plant. Number of fully open flowers per cluster at any one time: 6.5.

Flower description:

*Type.*—Solitary, zygomorphic, and bilabiate with nectar spur. Flowering is acropetally toward apex. Flowers have a slight sweet fragrance and are persistent.

*Flower size/aspect.*—Length: Approximately 1.7 cm. Width: Approximately 1.7 cm. Depth, including nectar spur: Approximately 1.2 cm. Aspect: Facing outward and upward.

*Petals.*—Quantity: Five per flower.

*Upper four petals.*—Fused at base forming a lip having two central linear lobes and one outer obovate lobe on each side. Lip width: 1.7 cm. Apex of all lobes: Obtuse. Margin of all lobes: Entire. Length of central lobes: Approximately 8 mm. Width of central lobes: Approximately 4 mm. Length of outer lobes: Approximately 8 mm. Width of outer lobes: Approximately 5 mm.

*Lower petal.*—Has two obovate lobes and is modified into a nectar spur. Length from palate: Approximately 8 mm. Petal apex: Emarginate. Petal margin: Entire. Width of lower petal: Approximately 1.1 cm. Spur length: 7 mm. Spur diameter at base: Approximately 2 mm. Spur diameter at tip: Approximately 1 mm. Spur texture: Puberulent. Spur color: 154D.

*Petal color.*—When first opening and when fully opened, the upper surface of all lobes is lighter than 155D with palate of 6A. Lower surface is lighter than 155D.

*Peduncle.*—Shape: Tetragonal. Strength: Strong. Surface texture: Densely pubescent. Angle to the stem: Acute. Length: Approximately 3.6 cm. Diameter: Approximately 1 mm. Color: 144A.

*Pedicel.*—Length: Approximately 1.1 cm. Diameter: Approximately 1 mm. Angle to stem: Acute. Strength: Good. Texture: Puberulent. Color: 144A.

*Bud.*—Shape: Ovoid with spur. Length: Approximately 5 mm. Diameter: Approximately 5 mm. Color: 154D.

*Calyx.*—Shape: Star. Width: Approximately 7 mm. Formed by five sepals fused at base. Sepal shape: Linear. Sepal margin: Entire. Sepal apex: Acute. Sepal length: Approximately 4 mm. Sepal width: Approximately 2 mm. Sepal texture: Upper surface: Glabrous. Lower surface: Densely pubescent. Sepal color: Both surfaces: 143B.

*Reproductive organs.*—Androecium: There are 4 stamens per flower — 2 are 3 mm in length, 2 are 2 mm in length. Filament shape: Curved. Filament color: 155D translucent. Anther shape: Oval. Anther length: 3 mm. Anther color: 166C. Amount of pollen: Abundant. Pollen color: 15A. Gynoecium: Number: One pistil per flower. Pistil length: 2 mm. Stigma length: Less than 1 mm. Stigma color: 150D. Style length: Less than 1 mm. Style color: 150C. Ovary diameter: 1.5 mm. Ovary color: 150B.

Seed and fruit production: Neither seed nor fruit production has been observed.

Disease and pest resistance: Resistance to pathogens and pests common to *Nemesia* has not been observed.

Hardiness zone: 'Balarcomwhit' is hardy in zones nine (9) and above.

What is claimed is:

1. A new and distinct cultivar of *Nemesia* plant named 'Balarcomwhit' substantially, as herein shown and described, which:

1. Exhibits white-colored flowers,
2. Forms medium green-colored foliage, and
3. Exhibits an upright and spreading growth habit.

* * * * *